United States Patent [19]

Pan

[11] 4,306,977

[45] Dec. 22, 1981

[54] CHROMATOGRAPHY DEVELOPING CHAMBER

[75] Inventor: Huo-Ping Pan, Lakewood, Colo.

[73] Assignee: The United States of America as represented by the Secretary of the Interior, Washington, D.C.

[21] Appl. No.: 211,556

[22] Filed: Dec. 1, 1980

[51] Int. Cl.³ .............................................. B01N 15/08
[52] U.S. Cl. .................................. 210/658; 210/198.3
[58] Field of Search .............................. 210/658, 198.3

[56] References Cited

U.S. PATENT DOCUMENTS

| | | | |
|---|---|---|---|
| 3,464,560 | 9/1969 | Clements et al. | 210/198.3 |
| 3,535,086 | 10/1970 | Baitsholts | 210/198.3 |
| 4,125,464 | 11/1978 | Burger et al. | 210/658 |

*Primary Examiner*—John Adee

*Attorney, Agent, or Firm*—William S. Brown; Donald A. Gardiner

[57] ABSTRACT

A chromatography developing chamber for developing thin layer or paper chromatographic materials comprising an elongated sleeve closed at one end, open at the other end and having a peripheral wall therebetween, such as a cylindrical sample tube. A ledge projecting inwardly from a peripheral wall of the sleeve is positioned adjacent the closed end to provide a surface for supporting the chromatographic material in the chamber. A liquid elution solvent fills the chamber from the closed end to a level below the ledge such that the chromatographic material on the ledge is supported out of contact with the solvent during a first stage of developing. The ledge permits the material to be readily displaced therefrom to fall into the solvent during a second stage of developing. The material may be displaced from the ledge by vibration, as by tapping the chamber, or by magnetic means.

13 Claims, 4 Drawing Figures

4,306,977

CHROMATOGRAPHY DEVELOPING CHAMBER

DESCRIPTION

TECHNICAL FIELD

The present invention relates to chromatography and, more particularly to a simple, compact chromatography developing chamber especially useful in thin layer and/or paper chromatography.

BACKGROUND ART

In typical thin layer or paper chromatographic processes a drop of the solution of chemical compound (s) to be identified is spotted near one end of the chromatography paper, glass plate or plastic film (chromatographic elements) and the end is immersed in an elution solvent (developer) which selectively separates the chemical compounds in the test drop, generally for comparision with known standards or established $R_f$ values of the constituents. Chromatographic elements can and have been developed in chambers ranging from beakers or test tubes or specially designed sandwich type chromatography chambers. However, except for special purpose chromatography chambers, such as for paper partition chromatography, development chambers now available carry out the developing process almost immediately after the chromatographic element is placed therewithin because the liquid solvent almost immediately is brought into contact with the element. It has now been found that solvent development is improved and good resolution, sharp spots and consistent $R_f$ values assured where the chromatographic elements are saturated with the solvent vapor prior to actual development by contact with the liquid solvent.

DISCLOSURE OF THE INVENTION

It is therefore an object of this invention to provide a chromatography developing chamber which permits solvent vapor saturation of the chromatographic element prior to development.

It is another object of the invention to provide such a chamber wherein solvent development can be accomplished immediately following solvent vapor saturation without need to open the chamber.

It is yet another object of the invention to provide such a chromatography chamber and method for its use which minimizes the amount of solvent needed, which minimizes the time required for solvent vapor saturation and development, which is easy to use and suitable for field use and which is readily adaptable to the evaluation of numerous test samples.

Other objects and advantages will become apparent from the following description and appended claims.

Briefly stated, the aforesaid objects are attained by a chromatography developing chamber especially useful for developing thin layer or paper chromatographic materials by a process where, in a first stage, the chromatographic elements are exposed to the solvent vapors for a time sufficient to achieve solvent vapor saturation thereof and, in a second stage, are placed in contact with the solvent to complete the developing process. The chamber comprises an elongated sleeve closed at one end and open at the opposite end. Exemplary of such a sleeve are conventional test tube type sample chambers. Preferably the open end is closable using a conventional screw cap, friction-fit plug or other suitable lid. Adjacent but spaced from the closed end of the sleeve is a ledge which projects into the sleeve or tube from the inner peripheral wall thereof. The portion of the sleeve or tube between the ledge and the closed end defines a receptacle for receiving the elution solvent. The ledge includes an upper support surface for supporting one end of the chromatographic element during the first or solvent vapor saturation stage of developing. The surface is configured in such a manner that the end of the element may readily be displaced therefrom into the solvent in the receptacle for the second stage of the developing process.

In one aspect of the invention, the solvent is placed in the receptacle to a liquid level below the ledge, the chromatographic element to be developed is inserted through the open end of the chamber until one end thereof rests on the ledge out of contact with the liquid solvent and the open end of the chamber is closed by a suitable lid. The element is then permitted to become saturated with solvent vapor. Following saturation, a gentle tap on the chamber or tube wall causes the element to fall off the ledge and to drop into the receptacle with one end immersed in the liquid solvent, at which point conventional chromatographic developing occurs.

In another aspect of the invention a ferromagnetic material is adhered to the chromatographic element, preferably in close proximity to the sample drop. Solvent vapor saturation proceeds as before. However, the element is removed from the ledge and placed into contact with the liquid solvent by applying a magnet to the outside peripheral wall of the chamber or tube. The magnetic field acting upon the ferromagnetic material draws the element off the ledge after which the element is placed or allowed to drop gently into the solvent in the receptacle.

BEST MODE FOR CARRYING OUT THE INVENTION

It has been found, as previously noted, that improved chromatographic developing, in terms of improved resolution, sharp spots and consistent $R_f$ values, results where the chromatographic elements, i.e. the paper strip, glass plate, plastic film, etc. containing a drop (or drops) of the solution to be investigated, are saturated with the solvent vapor prior to actual developing in contact with the liquid solvent. This improved developing is achieved in accordance with the present invention by a two stage process according to which the chromatographic element is maintained out of contact with the liquid solvent but exposed to the solvent vapors thereof during a first stage and, following saturation of the element by the solvent vapors, in placed, during a second stage, into contact with the liquid solvent.

Figure 1:
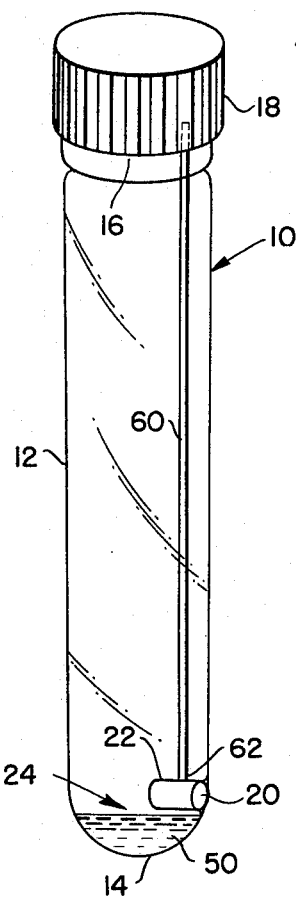
FIG. 1 is a perspective view of a chromatography developing chamber of the present invention showing a chromatographic element supported on the ledge during a first stage of developing.
Figure 2:
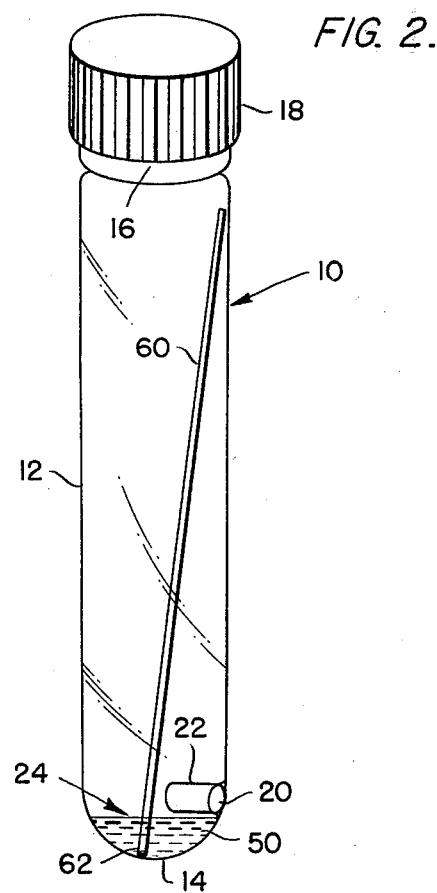
FIG. 2 is a perspective view of a chromatography developing chamber of the present invention showing the chromatographic element of FIG. 1 in contact with the elution solvent in the receptacle during a second stage of developing.

The improved process of the present invention is most conveniently practiced employing a simple, compact chromatography developing chamber such as is illustrated in FIGS. 1 and 2. With reference to these drawings there is shown an elongated sleeve-type chamber 10 in the form of a cylindrical tube 12 which is closed at one unitary and integral end 14 and open at the opposite end 16. End 16 is conveniently closable in any convenient manner, such as by use of a screw type cap 18 as illustrated. It will be appreciated that tube 12 may conveniently be a conventional test tube type sample holder. Alternatively, tube 12 may take any convenient form and have any convenient cross-sectional configuration. Since it is most usually desirable to watch the progress of a chromatographic process and since chromatographic eluents are typically strong solvents in nature, tube 12 should preferably be constructed of a transparent material which is unaffected by the chromatographic elution solvent, such as glass.

Adjacent to but spaced from the closed end 14 of tube 12 and projecting inwardly from the inner peripheral wall thereof is a ledge 20. Ledge 20 is preferably formed unitary and integrally with the peripheral wall of tube 12. Where tube 12 is formed of glass or other readily heat-deformable material, ledge 20 may conveniently be fabricated by heating the location of the ledge on the peripheral wall to red hot and then indenting it with a ledge-shaped pointed object. A receptacle 24 for elution solvent is defined in the tube volume between closed end 14 and ledge 20. When solvent 50 is added to tube 12 through open end 16, the upper liquid level of the solvent is always maintained below ledge 20. In this manner upper surface 22 of ledge 20 serves to support one end of a chromatographic element 60 out of contact with solvent 50 in receptacle 24. Typically, the upper surface 22 is flat and substantially horizontal to perform its dual function of supporting one end of the chromatographic element and permitting the element end to be readily displaced from ledge 20 to drop into solvent 50 within receptacle 24. Consistent with this dual function the configuration of the ledge may be altered as desired.

In a first stage of the chromatography developing process of the present invention an elution solvent 50 is added to receptacle 24 of tube 12 through open end 16 until a level below ledge 20 is reached. Then, a chromatographic element 60, which has been spotted in conventional manner with a drop of a sample to be investigated, is inserted through open end 16 of tube 12 with end 62 resting on and supported by the upper surface 22 of ledge 20. Tube 12 is then closed with screw cap 18. The configuration of the system is as shown in FIG. 1. During this stage the chromatographic element becomes saturated with the solvent vapors and the solvent atmosphere need never be disturbed throughout the developing process by removing the screw cap 18 for any reason.

The chromatographic element is permitted to rest on ledge 20 for a suitable length of time for saturation with the solvent vapor. After saturation, vibration of the tube, such as by a gentle tap on the outside peripheral wall of tube 12 in the general vicinity of ledge 20, causes end 62 of element 60 to slide off surface 22 and drop into solvent 50 in receptacle 24. At this point the second stage of the present developing process commences. This stage, involving direct contact between the chromatographic element and the solvent, is conventional in all respects. FIG. 2 clearly illustrates the position of chromatographic element 60 with end 62 in contact with solvent 50 during the second stage of developing.

Developing tube sizes of various dimensions, depending upon the investigation to be performed and the size of the chromatographic element, may be used. Thus, a convenient and commercially available tube is a screw-cap culture tube having a 16 mm diameter and a length of 150 mm. Chromatographic strips measuring $1 \times 10$ cm are particularly suitable for use with such tubes. The same size strips have been used in a screw-cap tube having a 20 mm diameter and a length of 129 mm. Ledge 20 was formed about 10 mm from closed end 14 and had a thickness from bottom to top of about 8 mm. Approximately 1 ml of solvent can conveniently be stored in the receptacle defined in the 20 mm diameter tube end below the bottom of ledge 20. Larger culture tubes, such as those having a dimension of 25 mm diameter by 200 mm length, can accomodate chromatographic elements (except thin paper) having dimensions of $15 \times 170$ mm, wide enough for two sample spots, one for the solution to be investigated and the other for a reference chemical. Still larger tubes or sleeves, e.g., 37 mm diameter by 200 mm length tubes, can be made which can accomodate two or more ledges for supporting chromatographic elements (except thin paper).

Figure 3:
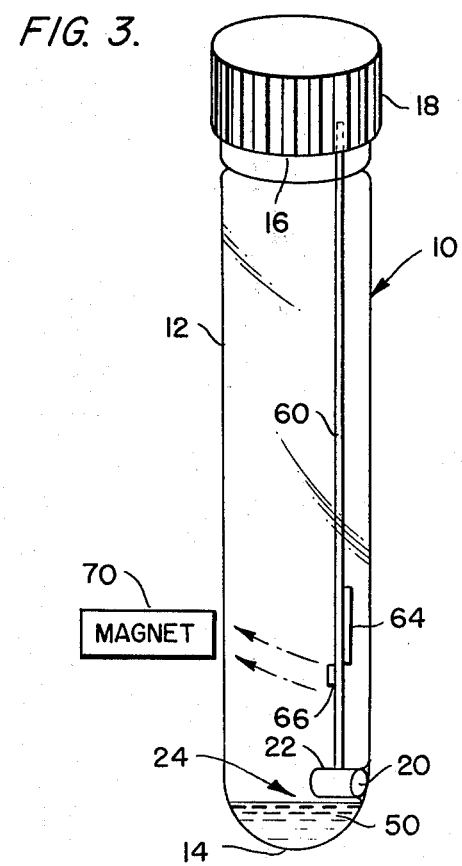
FIG. 3 is a perspective view of a chromatography developing chamber of the present invention showing a chromatographic element supported on the ledge during a first stage of developing and a ferromagnetic material adhered to the element under the influence of an applied magnetic field to displace the element from the ledge.
Figure 4:
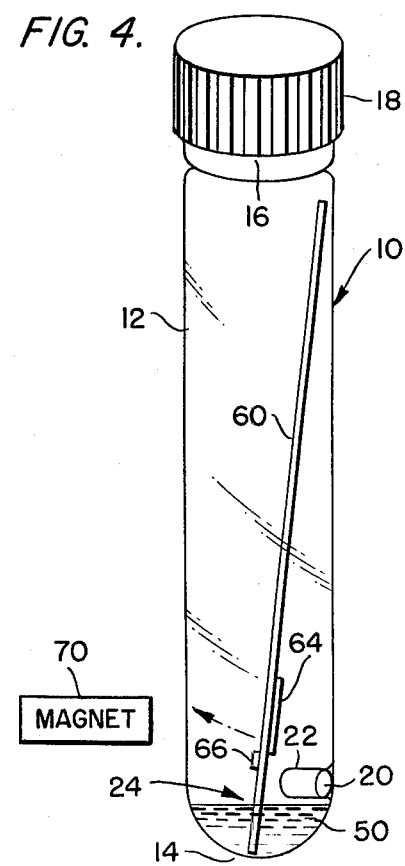
FIG. 4 is a perspective view of a chromatography developing chamber of the present invention showing the chromatographic element in FIG. 3 placed in contact with the elution solvent in the receptacle by an applied magnetic field during a second stage of developing.

In the method illustrated in FIGS. 3 and 4 the same chamber 10 as was described in connection with FIGS. 1 and 2 is employed. Chromatographic element 60 includes ferromagnetic material 64 adhered to the element, preferably in close proximity to the sample spot 66. In a particularly desirable configuration the ferromagnetic material 64 is adhered to the opposite face of the element approximately at the location of spot 66. Following solvent vapor saturation of the chromatographic element 60 in the first stage of developing, the end 62 of element 60 is lowered into contact with solvent 50 in receptacle 24 by applying a magnet 70 to the outer peripheral wall of tube 12 at a location opposite sample spot 66. The magnetic field created acting upon the ferromagnetic material 64 adhered to element 60 draws element 60 toward magnet 70, i.e., along and beyond upper surface 22 of ledge 20, until element 60 can be lowered into solvent 50 in receptacle 24. Alternatively, once element 60 clears the end of ledge 20 the magnet 70 can be removed and element 60 allowed to drop into solvent 50. FIG. 3 illustrates element 60 being drawn by magnet 70 along upper surface 22 of ledge 20. FIG. 4 illustrates element 60 with its end 62 lowered into solvent 50 in receptacle 24 by magnet 70 acting upon ferromagnetic material 64.

INDUSTRIAL APPLICABILITY

The practice of the present two stage chromatography developing method through use of the chromatography developing chamber 10 allows solvent vapor saturation of the chromatographic element inside a chamber before solvent contact development without opening the closed chamber during the development method. Such a process and apparatus assures good resolution, sharp spots and consistent $R_f$ values. At the same time the process and apparatus of the present invention employ relatively small volumes of eluent solvent, reduce the time necessary for solvent vapor saturation and development, permit large numbers of tubes to be used simultaneously and facilitate field chromatographic testing due to the easy portability of the chromatography developing chamber.

I claim:

1. A chromatography developing chamber for developing thin layer or paper chromatographic materials comprising:
   (a) an elongated sleeve closed at one end, open at the opposite end and having a peripheral wall therebetween for receiving said chromatographic material within said sleeve; and
   (b) means within said sleeve positioned adjacent said closed end for defining a receptacle to receive a liquid elution solvent and for supporting one end of said chromatographic material in said chamber, said means including a ledge projecting from said peripheral wall inwardly of said sleeve, said ledge including an upper support surface for supporting said chromatographic material out of contact with said solvent liquid during a first stage of developing and permitting said material to be displaced therefrom into said solvent in said receptacle during a second stage of developing.

2. A chamber, as claimed in claim 1, wherein said elongated sleeve comprises a cylindrical tube.

3. A chamber, as claimed in claim 2, wherein said closed end is unitary and integral with said peripheral wall.

4. A chamber, as claimed in claim 2, wherein said open end is closed by a removable cap.

5. A chamber, as claimed in claim 1, including a plurality of said means within said sleeve.

6. A chamber, as claimed in claim 5, including two said means within said sleeve.

7. A chromatography developing kit for developing thin layer or paper chromatographic materials comprising:
   (a) a chromatographic material for development, said material including ferromagnetic material adhered thereto;
   (b) a chromatography developing chamber, said chamber comprising an elongated sleeve closed at one end, open at the opposite end and having a peripheral wall therebetween for receiving said chromatographic material within said sleeve and means within said sleeve positioned adjacent said closed end for defining a receptacle to receive a liquid elution solvent and for supporting one end of said chromatographic material in said chamber, said means including a ledge projecting from said peripheral wall inwardly of said sleeve, said ledge including an upper support surface for supporting said chromatographic material out of contact with said solvent liquid during a first stage of developing and permitting said material to be displaced therefrom into said solvent in said receptacle during a second stage of developing; and
   (c) magnet means for applying a magnetic field to said chromatographic material supported on said upper support surface during said first stage of developing, the interaction between said magnetic field and said ferromagnetic material displacing said material from said surface into said solvent.

8. A developing kit, as claimed in claim 7, wherein said elongated sleeve comprises a cylindrical tube.

9. A developing kit, as claimed in claim 8, wherein said closed end is unitary and integral with said peripheral wall.

10. A developing kit, as claimed in claim 8, wherein said open end is closed by a removable cap.

11. A method of developing thin layer or paper chromatographic material comprising:
    (a) providing a closable developing chamber containing liquid elution solvent therein;
    (b) supporting said material within said chamber above said liquid solvent by means of a ledge projecting into said chamber from a peripheral wall thereof, said material being supported with one end thereof on said ledge;
    (c) closing said chamber;
    (d) exposing said material to the vapors of said solvent for a time sufficient to saturate said material with said solvent vapors; and
    (e) contacting said vapor-saturated material with said liquid solvent.

12. The method of claim 11 in which said vapor-saturated material is contacted with said liquid solvent by displacing said material from said ledge by vibrating said chamber.

13. The method of claim 11 in which said vapor-saturated material is contacted with said liquid solvent by displacing said material from said ledge by applying a magnetic field to said chamber.

* * * * *